United States Patent [19]

Sperling

[11] Patent Number: 5,080,485
[45] Date of Patent: Jan. 14, 1992

[54] METHOD FOR DETERMINING THE CONCENTRATION BY MEANS OF ATOMIC ABSORPTION SPECTROSCOPY

[75] Inventor: Michael Sperling, Sipplingen, Fed. Rep. of Germany

[73] Assignee: Bodenseewerk Perkin Elmer GmbH, Überlingen, Fed. Rep. of Germany

[21] Appl. No.: 481,410

[22] Filed: Feb. 16, 1990

[30] Foreign Application Priority Data

Feb. 24, 1989 [DE] Fed. Rep. of Germany ....... 3905782

[51] Int. Cl.$^5$ .................. G01J 3/00; G01N 21/72
[52] U.S. Cl. ................................... 356/315
[58] Field of Search ............... 356/315, 300, 36, 312

[56] References Cited

U.S. PATENT DOCUMENTS

| | | | |
|---|---|---|---|
| 3,705,770 | 12/1972 | Kashiki | 356/36 |
| 3,937,577 | 2/1976 | Dorsch | 356/312 |
| 4,620,284 | 10/1986 | Schnell et al. | 356/301 |

OTHER PUBLICATIONS

Maessen, "Direct Determination of Gold, Cobalt and Lithium in Blood Plasma Using the Mini-Massmann Carbon Rod Atomizer;" Analytical Chemistry, vol. 46, #11, 9/74, pp. 1445-1449.

Primary Examiner—F. L. Evans
Assistant Examiner—K. P. Hantis
Attorney, Agent, or Firm—Edwin T. Grimes; Thomas P. Murphy

[57] ABSTRACT

A method for determining concentration by means of atomic absorption spectroscopy, whereby the sample is supplied to a continuously operating atomizing device of an atomic absorption spectrometer by flow injection technique and generates a transient output signal of the atomic absorption spectrometer, comprises the method steps of supplying a calibration sample with a known concentration of the looked-for element to an atomic absorption spectrometer by flow injection technique, the concentration of the element looked-for in this sample being in a range of minimum standard deviation; storing the obtained transient calibration signal; supplying a sample which is to be analyzed and has an unknown concentration of the looked-for element to the atomic absorption spectrometer by flow injection technique and measuring a transient sample signal; forming signal ratios of the sample signal and the calibration signal at mutually corresponding predetermined moments of time; and determining the concentration of the looked-for element in the sample which is to be analyzed from these signal ratios.

11 Claims, 4 Drawing Sheets

METHOD FOR DETERMINING THE CONCENTRATION BY MEANS OF ATOMIC ABSORPTION SPECTROSCOPY

TECHNICAL FIELD

The invention relates to a method for determining concentration by means of atomic absorption spectroscopy, wherein a sample is supplied to a continuously operating atomizing device of an atomic absorption spectrometer by flow injection technique and generates a transient output signal of the atomic absorption spectrometer.

BACKGROUND OF THE INVENTION

Atomic absorption spectroscopy is a method for determining the concentration of a looked-for element in a sample which is to be analyzed. By an atomizing device, e.g., a burner with a flame, the sample which is to be analyzed is "atomized". Then, the components of the sample are present in an atomic state. A measuring light beam is passed through such an atomized sample. The measuring light beam is generated by a line emitting light source, e.g., a hollow cathode lamp. The spectral lines of the measuring light beam correspond to the resonant lines of the looked-for element. Therefore, the absorption to which the measuring light beam is subjected in the atomized sample depends on the number of atoms of the looked-for element and thus on the concentration of this element in the sample. The measuring light beam impinges on a detector which provides a corresponding signal. By means of a calibration sample this signal can be calibrated such that it provides the concentration of the sample.

The concentration of the looked-for element in the sample has to be within a certain measuring range. When the concentration is too small, the signal at the detector becomes too small and disappears in the noise. When the concentration becomes too large, the measuring light beam is entirely absorbed such that measurements are also impossible. Between these two points lies the measuring range wherein the signal of the detector depends in a substantially linear manner on the concentration of the looked-for element. Therefore, if required, the sample has to be diluted such that the concentration of the looked-for element is within this optimal measuring range.

It is known to supply samples to an atomizing device of an atomic absorption spectrometer by "flow injection". The sample is introduced into a loop of tubing. The atomizing device is supplied by a continuous carrier liquid flow. By means of a change-over valve (injection valve) the loop is connected into the carrier liquid flow. In this way the sample is supplied by the carrier liquid flow from the loop of tubing to the atomizing device. The sample forms a plug in the carrier liquid flow. On its way to the atomizing device, this plug diffuses to an approximately bell-shaped distribution of the concentration of sample liquid in carrier liquid.

Accordingly, the atomic absorption spectrometer provides a transient signal in the shape of an approximately bell-shaped peak. The shape of this peak is the same for all concentrations of the looked-for element within the linear measuring range. The peaks differ only by the ordinate which is proportional to the concentration.

By the publication of Olsen, Ruzicka and Hansen "Gradient Techniques In Flow Injection Analysis" in "Analytical Chimica Acta" 136 (1982) 101–112, particularly FIGS. 6 and 7 and the text referring thereto on page 108–109, a method for generating a family of calibration curves with different dilutions of the sample is known. Several calibration curves are measured in which the looked-for element is present in the different concentrations. Signal peaks result which have substantially the same waveform but different amplitudes. The signals are scanned at their descending slope of the signal peaks at different scanning times, each referred to the time of the signal maximum. Each of these scanning times provides a calibration curve which corresponds to another dilution of the sample. The signal of an unknown sample is scanned at such scanning time at which the amplitude of its signal peak is in the optimal, linear measuring range. Thus, the dilution of the sample is superseded by the selection of the scanning time. This is called "electronic dilution". This "electronic dilution" is also described in "Fresenius Zeitschrift für Analytische Chemie" (1988, 329:678–684).

By a publication of B. V. L'vov "Graphite Furnace Atomic Absorption Spectrometry on the Way To Absolute Analysis" in "J. Anal. At. Spectrom.", 3 (1988, 9–12), a method is known for determining the concentration of an element looked-for in a sample by means of atomic absorption spectroscopy in which the sample is electrothermally atomized. A sample is introduced into a graphite furnace. The graphite furnace is heated to a high temperature. Thereby, a "cloud of atoms" is generated within the graphite tube in which cloud the components of the sample are present in an atomic state. The measuring light beam is passed through the graphite tube. Here also, a bell-shaped, transient signal results. The sample is atomized whereby the signal increases and, thereafter, the atomic vapor is removed from the graphite furnace by an inert gas flow whereby the signal again decreases.

In the method described by L'vov two calibration solutions are used. An initial calibration solution comprises the looked-for element in a relatively low concentration although sufficiently far beyond the detection limit. This calibration solution generates a signal within the linear range of the atomic absorption spectrometer. The second calibration solution comprises the looked-for element in a concentration which is at the upper end of the detection range. The signal course obtained with the second calibration solution is compared point for point with the corresponding signal obtained with the initial calibration solution. If the atomic absorption spectrometer were to operate linearly throughout the entire detection range, the signals would behave at any time as the concentrations of the two calibration solutions. Using the divergency of the signal actually measured with the second calibration solution from the value calculated with a linear calibration curve taken as a basis, a calibration curve can be determined by regression calculation. By means of this calibration curve the signal course of an unknown sample can be linearized. From the linearized signal course either the peak level or the peak area can be determined for the signal evaluation.

DISCLOSURE OF THE INVENTION

It is the object of the invention to carry out a calibration with a single calibration solution in a method using the flow injection technique of the type mentioned above.

It is a further highly significant object of the invention to provide a method of the initially mentioned type which uses flow injection techniques and renders possible on-line operation of the atomic absorption spectrometer in a manner such that sufficiently precise concentration determination is enabled despite high sample throughputs.

According to the invention this object is achieved by the method steps:

(a) supplying a calibration sample with a known concentration of the looked-for element to an atomic absorption spectrometer by flow injection, the concentration of the element looked-for in this sample being in a measuring range in which this concentration can be determined with the least possible standard deviation, (b) storing the thus obtained transient calibration signal, (c) supplying a sample which is to be analyzed and has an unknown concentration of the looked-for element to the atomic absorption spectrometer by flow injection, (d) forming signal ratios from the data of the transient calibration signal and the transient sample signal at mutually corresponding, predetermined moments of time, and (e) determining the concentration of the looked-for element in the sample to be analyzed from the formed signal ratios.

Thus, only a single calibration solution with a known concentration of the looked-for element is required. The known concentration is selected such that the measured absorption including the peak maximum is within the measuring range in which this concentration can be determined with the least possible standard deviation.

Thereafter, a sample signal is measured of the sample to be analyzed. The calibration signal as well as the sample signal form a transient bell-shaped signal which is measured as a function of time under substantially identical flow injection conditions. The concentration of the looked-for element in the sample to be analyzed, then results immediately from the signal ratio of the sample signal and the calibration signal at corresponding moments of time.

Due to the formation of the signal ratios, the inventive method is not restricted to the linear measuring range of the atomic absorption spectrometer in which range only a relatively small number of measured data is available which are furthermore afflicted with a poor signal-to noise ratio. The inventive method which uses only a single calibration sample, processes a significantly higher number of measured data because the inventive method also encompasses the non-linear measuring range of the atomic absorption spectrometer, and permits a considerably increased measuring precision by virtue of the favorable signal-to noise ratio and the small standard deviations of the measured data located in this non-linear measuring range. Non-linearities can also be caused by matrix effects. Matrix effects depend mostly on the absolute concentration of the matrix and not on the ratio of the concentrations of the looked-for element and the matrix. Therefore, matrix effects can be reduced by diluting the sample. The transient signal, indeed, also comprises the information about many diluted samples, i.e., at measuring points which are temporally relatively far behind the peak maximum. However, in this range the signal-to-noise ratio is very disadvantageous and thus the standard deviation becomes excessive.

Advantageously, therefore, the invention contemplates subjecting the determined signal ratios as a function of the absorbance to a linear, preferably weighted linear regression analysis. In such a manner, there can be suppressed all those signal ratios having a standard deviation in excess of a predetermined threshold value. There is thus obtained during an on-line operation and by extrapolation to zero absorbance, a signal ratio which has a favorable standard deviation and which is practically independent of non-linearities in the measurement of absorbance and of matrix effects.

PREFERRED EMBODIMENT OF THE INVENTION

Figure 1:
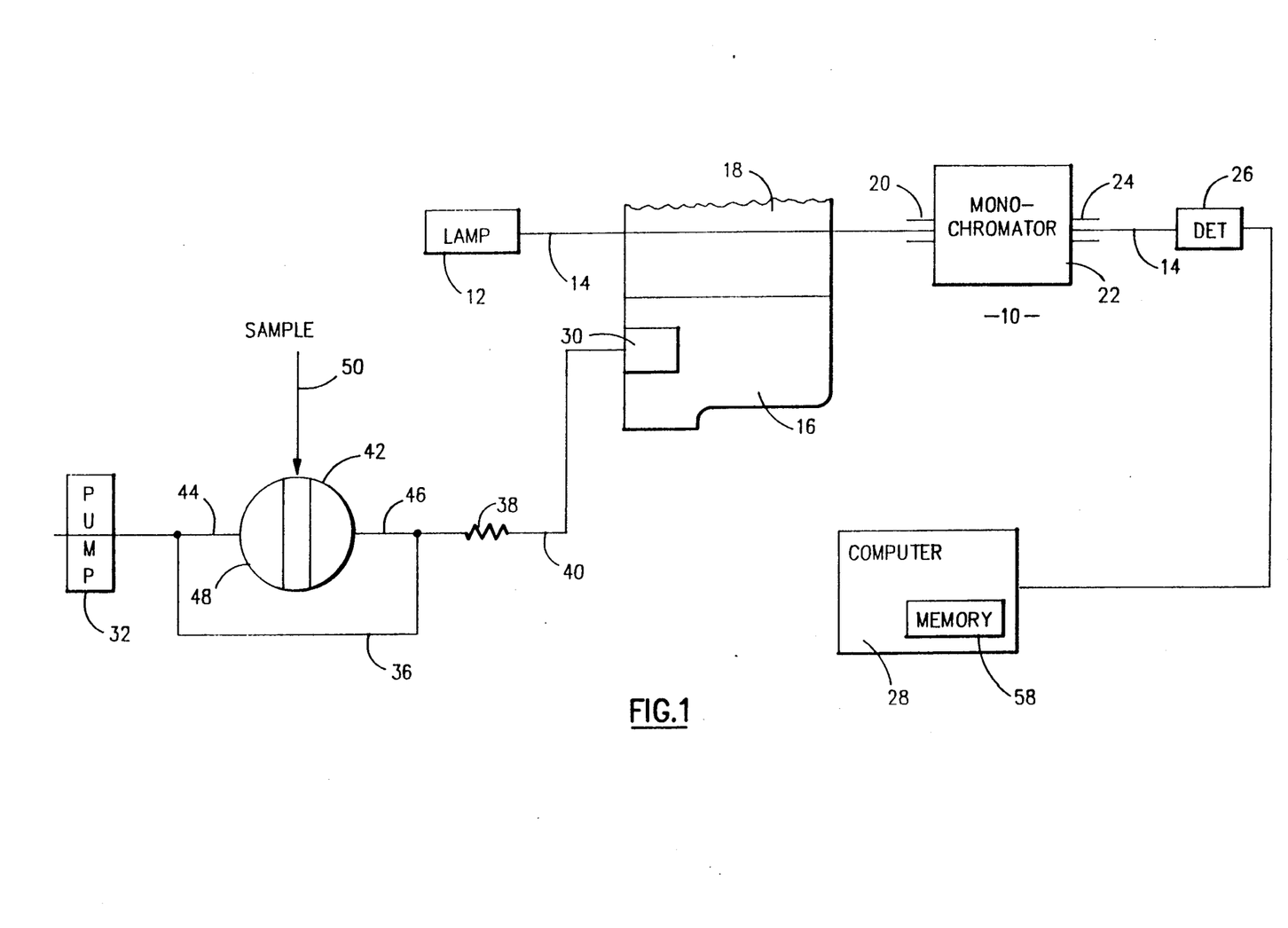
FIG. 1 shows schematically an atomic absorption spectrometer with a flame as atomizing device and sample supply by flow injection.

FIG. 1 illustrates a device for determining the concentration of a looked-for element in a sample to be analyzed by means of atomic absorption spectroscopy. The device comprises a very schematically illustrated atomic absorption spectrometer 10. The atomic absorption spectrometer 10 comprises a line-emitting light source 12 in the form of a hollow cathode lamp which emits a measuring signal. The atomizing device 16 is formed by a burner. A flame 18 burns on the burner. The measuring light beam 14 passes through the flame and impinges on the entrance slit 20 of a monochromator 22. Only a narrow spectral range around a certain line of the line spectrum emitted by the light source 12 passes through the monochromator 22 to the exit slit 24. The measuring light beam 14 emerging from the exit slit 24 impinges on a detector 26. The signal of the detector 26 is supplied to a computer 28. The computer 28 is programmed or designed in any other appropriate manner to perform the signal processing or evaluating operation described hereinbelow.

The burner 16 comprises a nebulizer 30. A carrier liquid flow is supplied to the nebulizer 30 by a hose pump 32 through a conduit 34, a bypass circuit 36, a mixing coil 38 and a conduit 40. The carrier liquid can be de-ionized water, for example. The bypass circuit 36 bypasses a change-over valve 42 (injection valve). The change-over valve 42 is connected parallel to the bypass circuit 36 with two connections 44 and 46 to the conduit 34. FIG. 1 shows the change-over or injector valve 42 in a position in which it shuts off the communication between the connections 44 and 46. A loop tubing 48 can be connected with the conduit 34 by the change-over valve 42 in its second position. In the illustrated first switching position a sample is introduced into the loop tubing as indicated by arrow 50. This can be a calibration sample containing a known concentration of the looked-for element or a sample which is to be analyzed and contains an unknown concentration of the looked-for element. When the change-over valve 42 is switched to its second switching position the sample is flushed out of the loop tubing 48 by the carrier liquid flow and is conveyed through the mixing coil 38 and conduit 40 to the nebulizer 30. Then the sample liquid is sprayed into the flame 18 and is atomized.

Therefore, in the flame the components of the sample are present in an atomic state. The measuring light beam 14 is attenuated by the atoms of that element the line spectrum of which is emitted by the light source 12. The attenuation of the measuring light beam 14 provides a detector signal.

On its way from the tubing loop 48 to the nebulizer the plug of sample substance is subject to a "dispersion"; the plug diffuses and forms a nearly bell-shaped concentration distribution. There thus occur in a sequence all concentrations from the concentration zero through a maximum value and back to zero. Correspondingly, time-dependent absorbances and signal variations of an approximately bell-shaped, slightly unsymmetrical shape result at the detector. Such signal courses are illustrated in FIG. 2 for two different concentrations.

Figure 2:
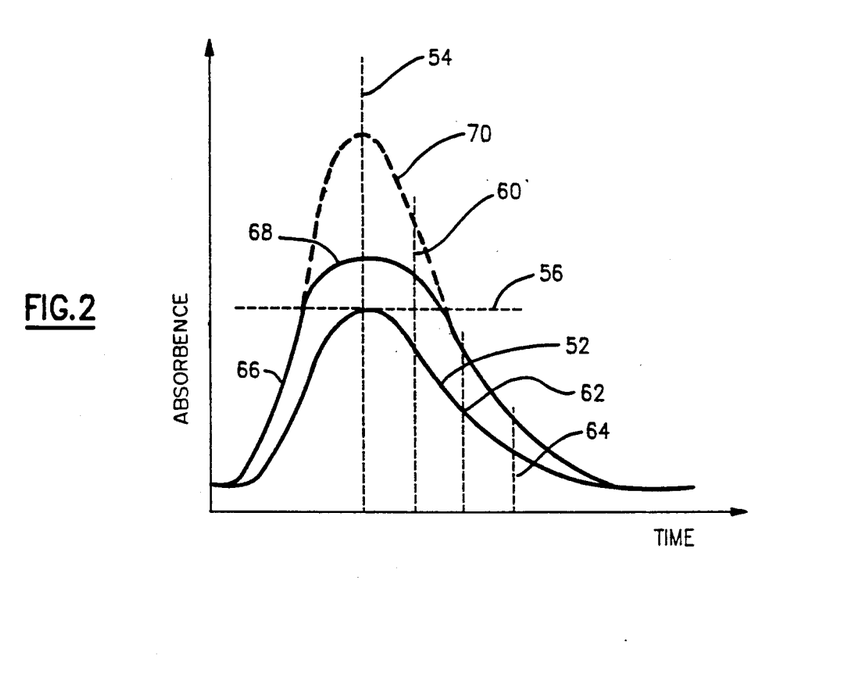
FIG. 2 shows, as a function of time, a signal course as it is obtained in the atomic absorption spectrometer shown in FIG. 1 with a calibration curve in the optimum measuring range and with a sample to be analyzed having a substantially higher concentration of the looked-for element.

In FIG. 2 numeral 52 designates a transient calibration signal, i.e., a signal course of signal at the detector 26. This signal course is obtained with a calibration sample of a known concentration of the looked-for element. The concentration of the looked-for element is selected such that the signal of the detector 26 is entirely within the measuring range in which the signals produced by the detector result in a minimum standard deviation of the determined concentrations. At the peak maximum, the time of which is indicated by a vertical line 54, the signal assumes a value which is characterized by the horizontal line 56. Below this line 56 is the desired measuring range in which the measured data have the least possible standard deviation. From the peak maximum the signal decreases. This means that the sample is more and more diluted with increasing distance from the peak maximum. The course of the signal is scanned at defined moments of time, for example, every 20 ms and stored in a memory 58 of the computer 28. The moments of time 60, 62, and 64 follow the moment of time 54 of the peak maximum and are here illustrated by the vertical lines 60, 62 and 64 in a simplified manner.

Then, in the same way, a sample which is to be analyzed, is passed through the tubing loop 48 and the nebulizer 30 into the flame and is atomized. There is thus obtained at the detector 26 a signal course which corresponds to a transient sample signal 66. The concentration of the looked-for element is assumed to be so high that the aforementioned measuring range of the minimum standard deviation below the line 56 is exceeded. Increases in the concentration above the value of the line 56 causes less precise measured data which have higher standard deviations and increase non-linearly and less with increasing concentration so that the signal course 66 is flattened in the area 68 around the peak maximum. Curve 70, for example, would represent a signal having a theoretical variation which would be proportional to the concentration in the sample to be analyzed.

Now, the concentration of the looked-for element in the unknown sample can be determined from the ratio of the signals below the line 56 at the moments of time 62 and 64. In this range the desired minimum standard deviation is guaranteed. For further improvement in the measuring precision, the calibration signal may form an average formed from a multiple number of, for instance, five transient calibration signals 52.

In the subsequently described, practical exemplary embodiment of the inventive method, a continuous sample throughput and an on-line evaluation of the transient sample signals is enabled. The transient calibration signal and the transient sample signal are measured under comparable flow injection conditions. Particularly due to the construction of the mixing coil 38, the flow injection system is devised in a manner such that there are obtained transient signals mostly symmetric relative to the maximum. The mixing coil 38 may be of the type as described, for example, by H. Engelhardt and U. D. Neue under the title "Reaction Detector With Three Dimensional Coiled Open Tubes In HPLC" in the Journal Chromatographia, Vol. 15, 1982, page 403.

Furthermore, a superposition of the calibration signal and the sample signal for determining the signal ratios can be carried out in a manner such that there is obtained a minimum difference between the signal ratios determined at the ascending flank and the descending flank of the signals. Also, by carrying out a weighted linear regression analysis all those signal ratios having unacceptably high standard deviations, can be suppressed and the determined signal ratios can be extrapolated to zero absorbance. In this manner, there are obtained concentration values which do not require working in the optimum operating range of the atomic absorption spectrometer and in which the influence of irregularities of the flow injection system, non-linearities and matrices are minimized.

Figure 3:
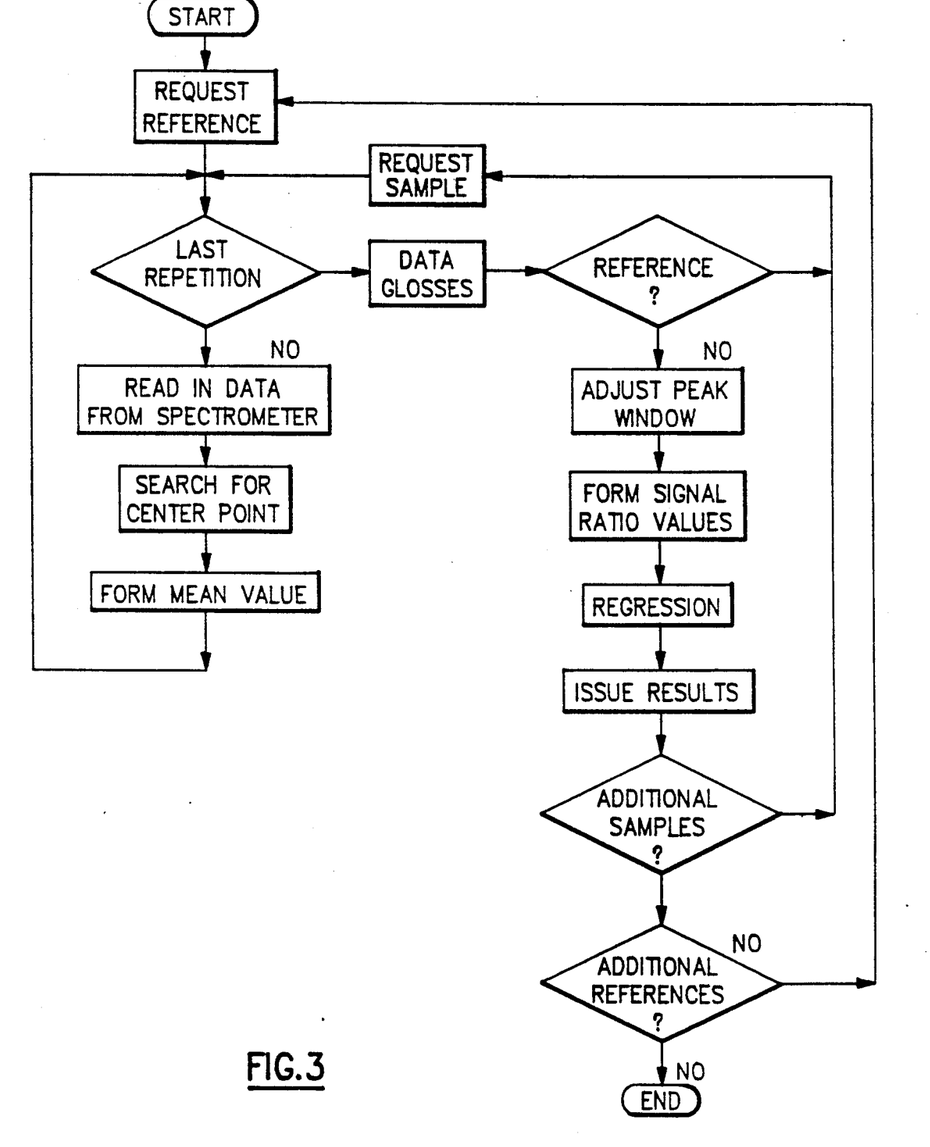
FIG. 3 is a flow diagram illustrating the evaluation of the data measured when carrying out the inventive method.

In the practical exemplary embodiment the atomic absorption of calcium is measured in aqueous solution (0.4 to 40 mg/l; doubly deionized water; pH 3 by nitric acid purified by sub boiling distillation) in the presence and in the absence of phosphate (Perkin-Elmer 3030 B atomic absorption spectrometer; calcium hollow cathode lamp operated at 15 mA; wavelength 422.7 nm, slit width 0.7 nm; standard air-acetylene burner; deuterium arc background correction). For processing the data, the spectrometer and its bidirectional RS-232 C interface board are connected via a serial interface to the computer 28 (IBM-AT compatible Epson PC-AX computer) which is programmed for the data evaluation by means of a QUICK-BASIC program of the type as illustrated by the data flow diagram shown in FIG. 3.

A Bifok 8410 flow injection system containing a 4-channel peristaltic pump, Bifok/Tekator V-100 sample injector and a HPLC pump (Perkin-Elmer Series 2; 3 ml/min) serves for flow injection. The mixing coil 38 comprises a three dimensional reactor made of tubes having 0.35 mm i.d. The volume of the sample loop was 100 ul.

When carrying out the measurement, the signal for actuating the switch-over or injector valve 42 also served as a starting signal for starting reception and processing of the measured data produced by the atomic absorption spectrometer 10. The measured data are taken at a time resolution of 20 ns and a quartic Savitzky-Golay filter filters and smoothes 25 points of measured data in the manner as described, for example, in the publication by A. Savitzky and M. J. E. Golay entitled "Smoothing and DIfferentiation Of Data By Simplified Least Squares Procedures", published in Analyt. Chem. 36, 1964; pages 1627-1639.

The total signal is integrated and a signal window for signal processing is set to the range of, for example, 0.5% to 99.5% of the total integrated signal. The center of gravity of the signal is, then, adjusted to a value at which the integrated signal has 50% of its total value. For further evaluation, the calibration signal and the sample signal are computationally compared such that the respective centers of gravity coincide. Thereafter, the precise relative position of the two signals is adjusted such that the sum of the differences between the signal ratios formed from the two signals on the ascending flank and the decending flank of the signals assumes a minimum value.

In this manner, the effect of synchronization errors between the atomic absorption spectrometer 10 and the flow injection system, of irregularities in the actuation of the switch-over or injector valve 42, and of fluctuations in the carrier liquid throughflow upon the signal evaluation are eliminated to a large extent.

After taking, for example, five calibration measurements, a calibration curve is produced by averaging the data or transient calibration signals obtained from the five calibration samples and serves as a basis for evaluating the transient sample signals obtained from samples to be analyzed for the analytical determination of calcium in the samples. Advantageously, the calibration signals are measured at calcium concentrations resulting in measured data located within the aforementioned range of minimum standard deviations.

The three dimensional reactor construction of the mixing coil 38 made of tubes having a narrow throughflow cross-sectional area, result in an only limited dispersion of the sample in the carrier liquid and thereby an improved precision in the measuring operation as a function of time. Therefore, a regression analysis in terms of a linear regression in accordance with the least square method can be carried out during the actual measurement in an on-line operation as a function of the variable signal-to-noise ratio, for instance, by transforming the scale from linear to logarithmic or by differently weighing the individual measured data. It is thereby possible to weigh the regression coefficients on the basis of their reciprocal variance without unfavorably affecting the course of the regression curve and while obtaining a random distribution of the regression residues.

Figure 4:
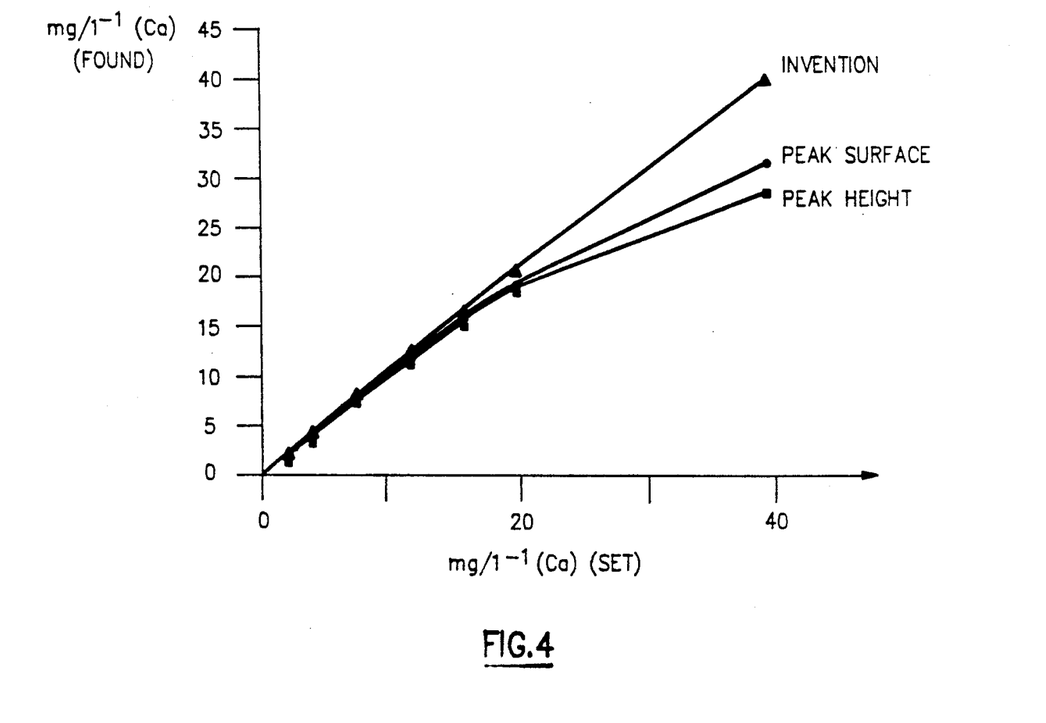
FIG. 4 is a graphic diagram showing a calibration curve determined according to the invention method in comparison with calibration curves determined by other methods.

Altogether, when carrying out the inventive method, there is obtained a significant improvement in the concentration determination in comparison with other methods relying, for example, upon peak area or peak height measurements. This is due to the fact that the calibration curve extends linearly through a much greater concentration range, particularly also widely outside the aforenoted range of minimum standard deviations. FIG. 4 shows that the calibration curve determined according to the inventive method, in fact, extends linearly through the entire concentration range from 0.4 to 40 mg/l calcium.

Figure 5:
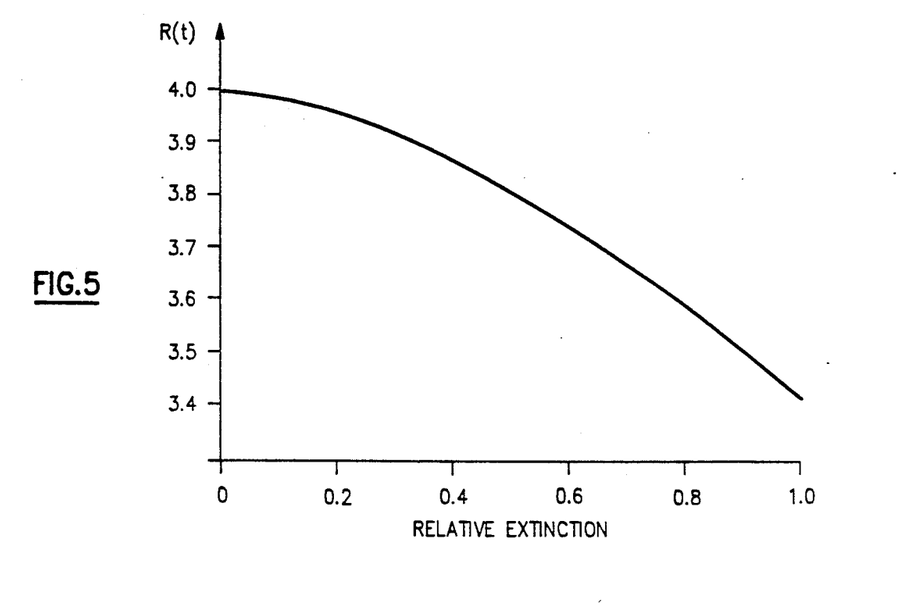
FIG. 5 is a graphic diagram illustrating the variation of the determined signal ratio as a function of relative absorbance in the absence of a matrix effect.

Furthermore, the inventive method permits determining the signal ratios R (t) by extrapolation from the non-linear measuring range of the atomic absorption spectrometer to the absorbance 0. In FIG. 5 this is illustrated with reference to a curve obtained from a pure calcium solution having a calcium concentration exceeding that of the calibration sample by a factor of, for example, four. The curve shows the determined signal ratio R (t) as a function of the relative absorption, i.e., the absorbance normalized to 1 at the maximum. It will be recognized that the measured signal ratio R (t) increasingly deviates from the theoretical value with increasing relative absorbance. It will also be recognized that the measured signal ratio R (t) increasingly approaches the theoretical value with decreasing relative absorbance and is substantially equal thereto in the region of low relative absorbance. In other words, the signal ratio extrapolated to zero absorbance is substantially identical with the theoretical value.

Therefore, in the absence of matrix effects, the signal ratio R (t) can be determined with high precision by extrapolation from the non-linear measuring range of the atomic absorption spectrometer. This explains that the calibration curve, as illustrated in FIG. 4, extends linearly through a very wide range of concentrations.

Figure 6:
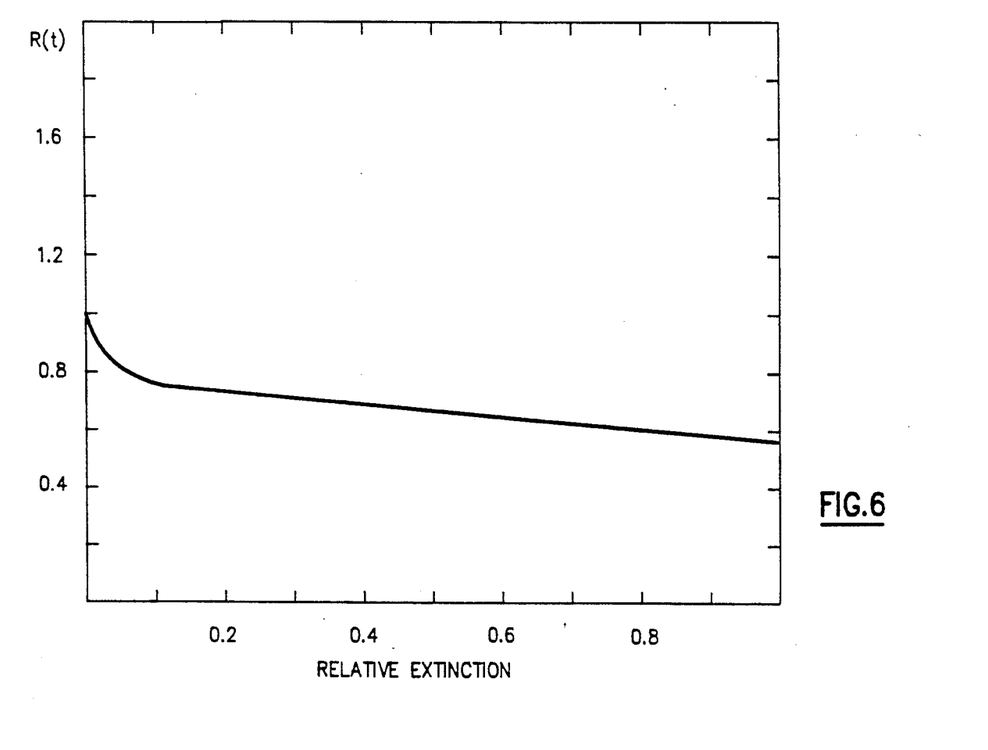
FIG. 6 is a graphic diagram illustrating the variation of the determined signal ratio as a function of relative absorbance in the presence of a matrix effect.

A further, specific advantage of the inventive method resides in the fact that matrix effects can be accounted for. As an example, FIG. 6 shows a curve representing the measured signal ratios R (t) as a function of relative absorbance at equal Calcium concentrations (12 mg/l) in the calibration sample and the sample to be analyzed in the presence of 0.01 M/l phosphate.

It will be recognized that there occurs already at low concentrations or low relative absorbances, a massive suppression of the measured signal. This suppression increases with increasing concentration or relative absorbance to a maximum at the peak maximum which frequently is relied upon in conventional signal evaluation methods. It will be further recognized that also in the presence of such matrix effect, extrapolation of the signal ratio R (t) to zero relative absorbance will result in the correct concentration ratio, namely the value 1 in the present case, although at less precision in comparison to the curve illustrated in FIG. 5. This reduced precision is a consequence of the increased slope of the curve at low relative absorbance due to the matrix effects.

The following table lists the calcium concentration found according to various measuring methods in the presence of phosphate:

Determination of Calcium in the Presence of Phosphate

| Measuring Sample | | Measured Calcium Concentration (mg/l) | | |
|---|---|---|---|---|
| Calcium (mg/l) | Phosphate (M/l) | Peak Height | Peak Area | Invention |
| 12 | 0.002 | 6.92 ± 0.20 | 7.30 ± 0.18 | 11.84 ± 0.84 |
| 12 | 0.01 | 6.84   0.12 | 7.25   0.18 | 11.62   0.68 |

It will be apparent from the foregoing table that, when using the known methods, the measurement is carried out at considerably higher precision but the found concentration widely deviates from the correct concentration. However, the inventive method, although operating at reduced precision when compared with the known methods, permits obtaining a measuring result which is equal to the correct value within the limits of error.

What is claimed is:

1. A method for determining concentration of an analyte in a sample by means of an atomic absorption spectrometer, comprising the steps of:

preparing a calibration sample containing a known concentration of an analyte and which concentration is in a measuring range of an atomic absorption spectrometer in which measuring range of this concentration is determined with the least possible standard deviation;

supplying a carrier liquid flow to atomizing means of said atomic absorption spectrometer;

injecting said calibration sample into said carrier liquid flow and thereby supplying said calibration sample to atomizing means of said atomic absorption spectrometer by flow injection;

storing a thus obtained transient calibration signal produced by the atomic absorption spectrometer;

injecting a sample containing an unknown concentration of the analyte into said carrier liquid flow and thereby supplying said sample containing said unknown concentration of the analyte to atomizing means of atomic absorption spectrometer by flow injection;

measuring a thus objected transient sample signal produced by said atomic absorption spectrometer;

forming signal ratios of the sample signal and the calibration signal at mutually corresponding, predetermined moments of time associated with said transient sample signal and said transient calibration signal; and determining the concentration of the analyte in said sample from said signal ratios.

2. The method as set forth in claim 1, further including the steps of:

scanning each one of said transient calibration signal and said transient sample signal at a predeterminate scanning frequency;

determining a predetermined window; and using scanned values of said transient calibration signal and said transient sample signal obtained within said predetermined window for determining the concentration of said analyte.

3. The method as set forth in claim 2, further including the steps of:

integrating each one of said transient calibration signal and said sample signal; and said step of determining said predetermined window entailing the step of determining a lower limiting value and an upper limiting value for integrating each one of said transient calibration signal and said transient sample signal.

4. The method as set forth in claim 3, wherein:

during said step of determining said lower limiting value and said upper limiting value for integrating each one of said transient calibration signal and said transient sample signal, setting substantially 0.5% of the total of each one of the integrated transient calibration signal and the integrated transient sample signal as said lower limiting value and substantially 99.5% of the total of each one of said integrated transient calibration signal and said integrated transient sample signal as said upper limiting value.

5. The method as set forth in claim 3, further including the steps of:

adjusting, for forming said signal ratios, each one of said transient calibration signal and said transient sample signal to a predetermined center of gravity within said predetermined window; and selecting, as said center of gravity, 50% of the total value of the respective integrated signal.

6. The method as set forth in claim 5, further including the steps of:

displacing relative to each other with respect to time, said transient calibration signal and said transient sample signal such that their respective centers of gravity coincide; and further displacing relative to each other with respect to time said transient calibration signal and said transient sample signal, starting from the coincidence of the respective centers of gravity, and thereby minimizing the difference between the signal ratios formed on the ascending flank and on the descending flank of said transient sample signal.

7. The method as set forth in claim 1, further including the step of:

subjecting the signal ratios as a function of the absorbance to a linear regression analysis and obtaining, as a result of the linear regression analysis, a signal ratio extrapolated to zero absorbance.

8. The method as set forth in claim 7, further including the steps of:

during said step of subjecting said signal ratios to said linear regression analysis, subjecting said signal ratios to a weighted linear regression analysis; and suppressing all signal ratios having a standard deviation exceeding a predetermined threshold value.

9. The method as set forth in claim 1, further including the steps of:

obtaining and storing at least two of said transient calibration signals;

averaging said at least two transient calibration signals; and using said arranged at least two calibration signals during said step of forming said signal ratios.

10. The method as set forth in claim 1, wherein:

said step of determining the concentration of the analyte from said signal ratios entails determining said signal ratios as a function of absorbance values measured by said atomic absorption spectrometer and extrapolating said signal ratios to zero absorbance in order to thereby obtain a signal ratio value corresponding to the ratio of the concentrations of the analyte in said sample and in said calibration sample.

11. The method as set forth in claim 1, wherein:

said steps of supplying said calibration sample and said sample containing the unknown concentration of the analyte includes supplying said carrier liquid flow containing said injected sample and said injected calibration sample to a nebulizer of a flame atomizer in said atomic absorption spectrometer.

* * * * *

UNITED STATES PATENT AND TRADEMARK OFFICE
CERTIFICATE OF CORRECTION

PATENT NO. : 5,080,485
DATED : January 14, 1992
INVENTOR(S) : Michael Sperling

It is certified that error appears in the above-identified patent and that said Letters Patent is hereby corrected as shown below:

Column 9, line 10, delete "of"

Column 9, line 49, after "said" insert --transient--

Column 10, line 44, delete "arranged" and insert --averaged--

Signed and Sealed this

Twenty-ninth Day of June, 1993

Attest:

MICHAEL K. KIRK

*Attesting Officer*   *Acting Commissioner of Patents and Trademarks*